United States Patent [19]

Arendt

[11] Patent Number: 5,169,834

[45] Date of Patent: Dec. 8, 1992

[54] COMPOSITIONS AND METHOD FOR REDUCING VIAL BREAKAGE DURING LYOPHILIZATION

[75] Inventor: Volker D. Arendt, Princeton, N.J.

[73] Assignee: American Cyanamid Company, Stamford, Conn.

[21] Appl. No.: 621,171

[22] Filed: Nov. 30, 1990

[51] Int. Cl.⁵ .................. A61K 37/36; A61K 47/02; C07K 3/12; F26B 5/06
[52] U.S. Cl. ............................ 514/8; 34/5; 514/21; 514/769; 530/427
[58] Field of Search .................. 34/5; 62/60, 100; 424/400, 680, 715, 717; 514/971, 8, 769, 21; 530/427, 399

[56] References Cited

U.S. PATENT DOCUMENTS

| | | | |
|---|---|---|---|
| 2,149,304 | 3/1939 | Masucci | 34/5 |
| 2,388,134 | 10/1945 | Flosdorf et al. | 34/5 |
| 4,273,762 | 6/1981 | McAleer et al. | 34/5 |
| 4,478,829 | 10/1984 | Landaburu et al. | 530/427 |
| 4,863,736 | 9/1989 | Azain et al. | 424/423 |
| 5,044,091 | 9/1991 | Ueda et al. | 34/5 |

FOREIGN PATENT DOCUMENTS 2758 3/1990 World Int. Prop. O. .......... 530/399

Primary Examiner—Jeffrey E. Russel
Attorney, Agent, or Firm—Peggy A. Climenson

[57] ABSTRACT

A composition containing a high concentration of a biologically active drug and a method for the use thereof to reduce vial breakage in a lyophilization process are disclosed.

12 Claims, No Drawings

COMPOSITIONS AND METHOD FOR REDUCING VIAL BREAKAGE DURING LYOPHILIZATION

BACKGROUND OF THE INVENTION

In the animal health industry the need to treat up to 500 animals with a single dosage preparation is a common requirement. For practical purposes, therefore, a high dosage package would be beneficial. A high dosage package consists of two parts, the formulated powder and saline solution, which are combined to produce a high dosage preparation. The ADD-Vantage ® packaging system, developed by Abbott Laboratories, is an example to be used for such high dosage formulations. The package consists of a small vial carrying the lyophilized powder and a nonbreakable plastic bag filled with saline. When both components are combined the injectionible preparation is complete.

The preparation of vials containing formulated powder is achieved by lyophilizing solutions of a biologically active drug, including proteins, peptides and polypeptides, in a vial. For economic reasons, it is important to maximize quantities of formulated powder in each vial which makes it necessary to work with high drug concentrations and high fill volumes. High fill volumes and high drug concentrations, however, have been shown to produce excessive vial breakage during the lyophilization process.

It is an object of this invention to provide a composition containing a biologically active drug and a method for the preparation of formulated powder by lyophilizing highly concentrated solutions in highly filled vials without breakage.

A further object of this invention is to provide a package system consisting of the vials containing formulated powder and a container filled with formulated saline solutions which, upon reconstitution, will produce a solution of proper concentration required, for example, in injectible dosage forms.

SUMMARY OF THE INVENTION

The present invention discloses compositions of biologically active drugs including proteins, peptides and polypeptides in the presence of buffer salts which overcomes vial breakage during lyophilization of concentrated solutions in highly filled vials. A suitable amount of the biologically active drug is dissolved in an aqueous buffer solution and lyophilized without suffering excess vial breakage, producing a powder with good free flowing characteristics which is important for the reconstitution step.

The invention also demonstrates that reconstituted solutions for injection can be further modified by placing additional buffer salts in the saline solution used for reconstitution. This provides for a mechanism to prepare solutions of any desired buffer concentration without exceeding the critical concentration for low vial breakage during lyophilization.

DETAILED DESCRIPTION OF THE INVENTION

The present invention is directed to a composition of a biologically active drug with buffer salts and a method to use highly concentrated solutions in highly filled vials during lyophilization without suffering excessive vial breakage. In the present invention, a suitable amount of the biologically active drug is dissolved in an aqueous solution containing buffer salts. The solution is lyophilized to yield formulation powder. Recommended concentrations of biologically active drug are between about 14.5 and 18.0 weight/volume percent and buffer salts range from 0 to about 5.3 weight/volume percent, preferably about 0.1 to 4.2 weight/volume percent. After lyophilization, the powder composition is about 81 to 96.5 weight/weight percent biologically active drug and about 0.56 to 19 weight/weight percent buffer salt. In a preferred embodiment of the present invention the buffer system after lyophilization comprises about 0.1 to 9.5 weight/weight percent sodium carbonate and about 7.6 to 18.8 weight/weight percent sodium bicarbonate with the total salt concentration not exceeding about 19 weight/weight percent. The lyophilized powder is reconstituted, as part of a two component package, by pouring it from the vial into the formulated saline solution producing a solution for injection with a pH in a range of about 7.0 to 9.0. Surprisingly, it was found that in the absence of any buffer salts, flowability of the lyophilized product is hampered and reconstitution of the biologically active drug is impeded. Thus, by lyophilizing biologically active drug in the presence of buffer salts, a product allowing easy transfer from vial to formulated saline solution is accomplished.

In the preferred embodiment of the present invention, the concentration of the biologically active drug to be lyophilized is about 18 percent, the concentration of buffer salts is in a range of about 0.65 to 3.2 percent, the size of the lyophilization vial (ADD-Vantage ® Super Bottom*) is 24 milliliters and the fill volume is as high as 17.5 ml (73 percent capacity). The preferred lyophilized product composition comprises about 84.5 to 85.2 weight/weight percent of biologically active drug, about 0.1 to 7.6 weight/weight percent sodium carbonate and about 7.6 to 15.1 weight/weight percent sodium bicarbonate, with the total salt concentration not exceeding 15.2%.

*Wheaton 24cc4705-B20, Super Bottom Vantale vial w/double lead ACME thread finish NS-33.

Biologically active drugs suitable for administration in the compositions of the invention include growth hormones, somatotropins, growth factors, and other biologically active fragments and analogs and derivatives thereof. Preferred drugs include bovine, ovine, equine, procine, avian and human growth hormones, and encompass those which are of natural, synthetic recombinant or biosynthetic origin.

Formulated saline solutions may include preservatives, antioxidants, buffer salts, stabilizers and other commonly used excipients known in the art.

Buffer systems that may be used in this invention are well-known in the art. Examples of types of buffer systems that may be used in the present invention are illustrated in *Methods in Enzymology*, ed. Sidney P. Colowick and Nathan O. Kaplan, Academic Press, Vol. 1 pp. 143–145, 1963, and include the following non-limiting examples:

Monobasic sodium phosphate/dibasic sodium phosphate
Tris acid maleate/sodium maleate
Sodium barbital/hydrochloric acid
Tri(hydroxymethyl) aminomethane/hydrochloric acid salt
Boric acid/borax
2-amino-2-methyl-1,3 propanediol/hydrochloric acid salt
Sodium carbonate/sodium bicarbonate The first step in the novel method of the present invention is to dissolve a suitable amount, which may be up to about 180 grams per liter, of a biologically active drug which includes proteins, peptides or polypeptides, into an aqueous solution containing buffer salts.

The next step in the present invention is to lyophilize the biologically active drug and buffer salt solution to produce a lyophilized product.

The lyophilized product is then dissolved in a saline solution under aseptic conditions as provided by the ADD-Vantage ® package and the pH of the reconstituted solution is in a range of about 7.0 to 9.0, preferably about 8.25 to 8.35. Adjustments and control of pH are accomplished by adding proper quantities of buffer salts to the saline solution in the bag. In a preferred embodiment the reconstituted product which is used as a daily injectable composition comprises about 1.0 to 7.0 weight/volume percent biologically active drug, about 0.1 to 0.65 weight/volume percent sodium carbonate, about 0.3 to 1.6 weight/volume percent sodium bicarbonate and about 0.85 weight/volume percent sodium chloride. In a more preferred embodiment the daily injectable composition comprises about 1.26 percent biologically active drug, about 0.85 weight/volume percent sodium chloride, about 0.13 weight/volume percent sodium carbonate and about 0.32 weight/volume percent sodium bicarbonate.

The present invention is further illustrated by the following non-limiting examples.

EXAMPLE 1

Lyophilized Product

The solution is prepared according to the following formulation:
BST (Tech.) 145
Sodium Carbonate 7.7 g
Sodium Bicarbonate 81.3 g
Water f. Injection qs 1000 ml Buffer salts are dissolved in approximately 800 ml of water for injection (WFI), bovine somatotropin (BST) is added and stirred into solution. The volume is adjusted to 1000 ml and the solution is filtered through a prefilter to remove coarse impurities followed by filtration through 0.45 and 0.22 micron membranes. The clear solution is collected and metered accurately into fifty 24 ml ADD-Vantage ® vials filled to a volume of 17.5 ml (73% capacity). The vials are covered with lyophilization stoppers and sent to the freeze dryer. Vials are lyophilized following the cycle described below:

a. Freeze dryer is charged with filled vials at room temperature.
b. Dryer is closed and cooled to −45 deg C.
c. Temperature is held at −45 deg C. for 3 hours until vials are frozen.
d. Vacuum is applied and held at 22 microns.
e. Shelf temperature is set to −20 deg C. for 16 hours.
f. Shelf temperature is set to +15 deg C. for 21 hours.
g. Shelf temperature is raised to 25 deg C. for 3 hours.
h. The batch is held between 20-25 deg C. for 5 hours.
i. Vacuum is broken with nitrogen and bottles are sealed.
j. Vials are removed from the freeze dryer..
k. Vial breakage is recorded.

No breakage was observed after lyophilization.

EXAMPLE 2

Lyophilized Product

The solution is prepared according to the formulation below:
BST (Tech.) 145 g
Sodium Carbonate 15.4 g
Sodium Bicarbonate 36.5 g
Water f. Injection qs 1000 ml The ingredients are dissolved and the solution is treated as described in Example 1. The experiment produced 36 broken vials out of a total of 50 vials, or 72% breakage.

EXAMPLE 3

Lyophilized Product

Using the procedure described in Example 1, keeping the concentration of BST (Tech.) at 145 grams, and varying the concentration of buffer salts, the following data is obtained and reported in Table 1.

EXAMPLE 4

Lyophilized Product

The solution is prepared according to the formulation below:
BST (Tech.) 180 g
Sodium Carbonate 9.6 g
Sodium Bicarbonate 22.7 g
Water f. Injection qs 1000 ml The ingredients are dissolved and the solution is treated as described in Example 1. The experiment produced no broken vials.

EXAMPLE 5

Lyophilized Product

The solution is prepared according to the formulation below:
BST (Tech.) 180 g
Sodium Carbonate 14.5 g
Sodium Bicarbonate 14.5 g
Water f. Injection qs 1000 ml Ingredients are dissolved and the solution is treated as described in Example 1. The experiment produced no broken vials.

EXAMPLE 6

Lyophilized Product

Using the procedure described in Example 1, keeping the concentration of BST (Tech.) at 180 grams, and varying the concentration of buffer salts, the following data is obtained and is reported in Table 2.

EXAMPLE 7

Daily Injectable composition

The lyophilized product of Example 4 consists of 3.15 g BST (Tech), 0.17 g sodium carbonate and 0.4 g sodium bicarbonate per vial. The vial content is reconstituted by adding to a formulated saline bag containing 250 ml or 0.85% sodium chloride, 0.064% sodium carbonate and 0.16% sodium bicarbonate using the following procedure:

1. Screw threaded neck of sealed vial into the receptacle of the bag.
2. Remove seal of vial inside bag by manipulating from the outside through the bag wall.

3. Drop lyophilized powder into saline solution in bag.
4. Force solution back into glass vial to remove and dissolve all traces of BST.

The final injectable solution is composed to 1.26% BST, 0.13% sodium carbonate, 0.33% sodium bicarbonate and 0.85% sodium chloride. This solution is applied at a dose level of one milliliter per injection.

TABLE 1

14.5% BST Solution
Formulation of Solutions with Different Buffer Salt
Concentrations at Constant Level of BST

| LYOPHILIZATION SOLUTION | | | | | | |
|---|---|---|---|---|---|---|
| BST (Tech.) (g/l) | 145 | 145 | 145 | 145 | 145 | 145 |
| Sodium Carbonate (g/l) | 0 | 1.54 | 7.7 | 10.0 | 13.1 | 15.4 |
| Sodium Bicarbonate (g/l) | 0 | 3.65 | 18.3 | 23.8 | 31.1 | 36.5 |
| POWDER COMPOSITION AFTER LYOPHILIZATION | | | | | | |
| BST (TECH.) (W/W %) | 100 | 96.5 | 84.8 | 81.1 | 76.6 | 73.6 |
| Sodium Carbonate (W/W %) | 0 | 1.03 | 4.50 | 5.59 | 6.92 | 7.82 |
| Sodium Bicarbonate (W/W %) | 0 | 2.43 | 10.7 | 13.3 | 16.44 | 18.54 |
| Total Buffer Salts (W/W %) | 0 | 3.5 | 15.2 | 18.9 | 23.4 | 26.4 |
| BREAKAGE (%) | 0 | 0 | 0 | 6 | 80 | 72 |

As can be seen from the above data, vial breakage increases as total buffer concentration increases.

TABLE 2

18% BST Solution
Formulation of Solutions with Different Buffer Salt
Concentrations at Constant Level of BST

| LYOPHILIZATION SOLUTION | | | | | | | |
|---|---|---|---|---|---|---|---|
| BST (Tech.) (g/l) | 180 | 180 | 180 | 180 | 180 | 180 | 180 |
| Sodium Carbonate (g/l) | 0 | 1.92 | 14.5 | 9.65 | 12.4 | 16.2 | 19.1 |
| Sodium Bicarbonate (g/l) | 0 | 4.55 | 14.5 | 22.7 | 29.5 | 38.6 | 45.5 |
| POWDER COMPOSITIONS AFTER LYOPHILIZATION | | | | | | | |
| BST Tech. (W/W %) | 100 | 96.5 | 86.1 | 84.8 | 81.1 | 76.7 | 73.6 |
| Sodium Carbonate (W/W %) | 0 | 1.03 | 6.9 | 4.5 | 5.6 | 6.9 | 7.8 |
| Sodium Bicarbonate (W/W %) | 0 | 2.44 | 6.9 | 10.7 | 13.3 | 16.4 | 18.6 |
| Total Buffer Salts (W/W %) | 0 | 3.5 | 13.8 | 15.2 | 18.9 | 23.3 | 26.4 |
| BREAKAGE (%) | 0 | 0 | 0 | 0 | 2 | 52 | 68 |

As can be seen from the above data, vial breakage increases as total buffer concentration increases.

What is claimed is:

1. A lyophilized product composition which comprises about 81 to 96.5 weight/weight percent of a biologically active drug and a buffer system, wherein the buffer system comprises about 0.1 to 7.6 weight/weight percent sodium carbonate and about 7.6 to 15.1 weight/weight percent sodium bicarbonate with the total buffer system concentration not exceeding 15.2 weight/weight percent.

2. The composition according to claim 1, wherein the biologically active drug is bovine or porcine somatotropin.

3. The composition according to claim 1, wherein the biologically active drug is recombinantly derived bovine or porcine somatotropin.

4. The aqueous daily injectable composition which comprises about 1.0 to 7.0 weight/volume percent biologically active drug, about 0.1 to 0.65 weight/volume percent sodium carbonate, about 0.3 to 1.6 weight/volume percent sodium bicarbonate and about 0.85 weight/volume percent sodium chloride.

5. An aqueous daily injectable composition which comprises about 1.26 weight/volume percent biologically active drug, about 0.85 weight/volume percent sodium carbonate and about 0.32 weight/volume percent sodium bicarbonate.

6. The composition according to claim 5 wherein the biologically active drug is bovine or porcine somatotropin.

7. The composition according to claim 5 wherein the biologically active drug is recombinantly derived bovine or porcine somatotropin.

8. A method of reconstituting a lyophilized product to produce a daily injectable composition according to claim 4:
   (a) dissolving the lyophilized product in a reconstituting solution; and
   (b) adding quantities of buffer salts sufficient to adjust the pH of the daily injectable composition to a range of about 7.0 to 9.0.

9. The method according to claim 8 wherein the reconstituting solution comprises sodium chloride and buffer salts sufficient to bring the daily injectable composition to about 1.26 weight/volume percent biologically active drug, about 0.85 weight/volume percent sodium chloride, about 0.13 weight/volume percent sodium carbonate and about 0.32 weight/volume sodium bicarbonate.

10. The method according to claim 8 wherein the reconstituting solution comprises buffer salts in an amount sufficient to adjust the pH of the daily injectable composition to a range of about 7.0 to 9.0.

11. A method for reducing vial breakage during lyophilization of a biologically active drug which comprises:
   (a) dissolving a suitable amount of the biologically active drug in a buffer salt solution to form a second solution wherein the concentration of buffer salts is about 0.1 to 4.2 weight/volume percent;
   (b) transferring the second solution to a lyophilizing vial; and
   (c) lyophilizing the second solution to produce a lyophilized product wherein the lyophilized product comprises about 81 to 96.5 weight/weight percent of the biologically active drug, about 0.1 to 9.5 weight/weight percent sodium carbonate and about 7.6 to 18.8 weight/weight percent sodium bicarbonate and wherein the total salt concentration does not exceed 19 weight/weight percent.

12. The composition according to claim 11 wherein the biologically active drug is bovine or procine somatotropin.

* * * * *